United States Patent [19]

Daftary

[11] Patent Number: 5,035,619
[45] Date of Patent: Jul. 30, 1991

[54] ANATOMICAL RESTORATION DENTAL IMPLANT SYSTEM WITH IMPROVED HEALING CAP AND ABUTMENT

[76] Inventor: Fereidoun Daftary, 50 N. La Cienega Blvd., #206, Beverly Hills, Calif. 90211

[21] Appl. No.: 577,923

[22] Filed: Sep. 5, 1990

Related U.S. Application Data

[63] Continuation-in-part of Ser. No. 424,901, Oct. 20, 1989.

[51] Int. Cl.$^5$ .............................................. A61C 8/00
[52] U.S. Cl. .................................... 433/173; 433/174
[58] Field of Search ............... 433/169, 171, 172, 173, 433/174, 175, 176

[56] References Cited

U.S. PATENT DOCUMENTS

| | | | |
|---|---|---|---|
| 4,416,629 | 11/1983 | Mozsary et al. | 433/173 |
| 4,636,216 | 1/1987 | Tatum | 433/173 |
| 4,758,160 | 7/1988 | Ismail | 433/173 |
| 4,826,434 | 5/1989 | Krueger | 433/174 |
| 4,872,839 | 10/1989 | Brajnovic | 433/173 |

FOREIGN PATENT DOCUMENTS

0288446 10/1988 European Pat. Off. ............ 433/173

*Primary Examiner*—Cary E. Stone
*Attorney, Agent, or Firm*—Thomas I. Rozsa

[57] ABSTRACT

A system and method is provided for implanting tooth analogues in the jawbone resulting in aesthetically and functionally desirable gingival tissue contours after restoration. The system permits modification and adaptation of the tooth analogue to meet intraoral demands in a manner similar to that used in the preparation and restoration of natural teeth. The system comprises a standard fixture and cover screw passed through opened gingival tissue and implanted in the jawbone. After the osseointegration of the fixture, the gingiva is reopened, the cover screw removed and a healing cap having a predetermined contour, is attached to the fixture. The reopened gingiva re-heals in a shape determined by the contour of the healing cap. The healing cap is then removed and replaced by an abutment having an emergence profile matching that of the healing cap. An immediate snug fit between the gingival tissues and the abutment is thereby provided at the time of connection of the abutment to the fixture. A crown is removably attached to the abutment by a screw extending through the side of the crown into the abutment. An improved version of the healing cap is a healing cap created in two portions so that one portion around which gingiva tissue regrows remains in the patient and only a second upper portion is removed, and an improved abutment which is engageable with the portion of the healing cap left in the patient is used for the abutment about which the crown is removably attached.

17 Claims, 3 Drawing Sheets

ANATOMICAL RESTORATION DENTAL IMPLANT SYSTEM WITH IMPROVED HEALING CAP AND ABUTMENT

This is a continuation-in-part of co-pending application No. 07/424,901 filed Oct. 20, 1989, pending.

BACKGROUND OF THE INVENTION

1. Field of the Invention

The present invention relates generally to the field of dental implants and in particular to a system providing a tooth analogue and a gingival tissue healing cap which results in a restoration having tissue-implant profiles similar to that of a natural tooth and its surrounding gingiva. The present invention also relates to fitting a tooth with a temporary crown and final prosthesis after the initial implant structure has been inserted and the surrounding tissue has healed.

2. Description of the Prior Art

Many systems have been proposed for rigidly fixing metal or ceramic materials to the alveolus of a human mandible or maxilla in an effort to provide a long term replacement for lost teeth. Early systems were successful for only limited periods of time and were eventually rejected as foreign bodies. Later systems, as described by U.S. Pat. Nos. 3,589,011 to Sneer, 3,797,113 to Brainin, 3,979,828 to Taylor, 4,324,550 to Reuther et al., and 4,416,679 to Mozsary et al., have proven to offer long term success by providing rigid anchorage in the supporting bone. Intraoral restoration of such ossointegrated devices has been accomplished with many different systems that modified the original attempts. Such modifications have been described in U.S. Pat. Nos. 4,780,080 to Harras, 4,713,003 to Symington et al., and 4,657,510 to Gittlemen. However, these restorative systems have required biologic and aesthetic compromises. The interface between an implant and its surrounding gingival tissue is often insufficiently close to prevent food and bacteria from entering this area. Such foreign matter can cause chronic infection and bone loss, resulting in eventual loss of the implant. Implants in current use have a round root form dimensionally different from that of a normal tooth root morphology. This makes aesthetic restoration difficult and impedes the development of a natural soft gingival tissue contour.

There exists a need for a dental implant system providing an implant root and gingival tissue interface having an improved resistance to bacterial infection and providing a contour more nearly approximating that of a natural tooth and its surrounding tissue.

In addition, removal of the transepithelial sleeve and/or healing caps to fit a temporary crown and then a permanent crown requires removal of the entire abutment/or healing cap structure which causes damage to the surrounding tissue including apical migration of the tissue and in turn necessitates additional healing time. There exists a further need for a dental implant system which permits a temporary crown and then a permanent crown to be fitted and implated without requiring that the temporary abutment and/or healing caps be removed.

SUMMARY OF THE PRESENT INVENTION

The invention provides a system and a method for implanting tooth analogues in the alveolus of the jawbone. The emergence profile of the analogue more closely matches that of a natural root and the system provides a tight fit between the analogue and the gingiva upon instllation of a crown or other tooth replacement.

The system comprises an implantable fixture having proximal and distal end portions, the proximal end portion having means for being implanted through opened gingival tissue into the alveolus of the jaw bone, the distal end portion being accessible from the outer surface of the jaw bone. The fixture contains a hollow interior beginning with an opening in the distal end portion and extending towards the proximal end portion. The hollow has threads along at least a portion of its length.

The invention utilizes a cover screw for sealing the hollow portion of the fixture during the time the jaw bone is growing about the fixture. After osseointergration of the fixture, the gingiva is reopened and the cover screw is removed and replaced by a healing cap. Having the same contour permits the abutment to tightly fit the healed opening in the gingival tissue upon engagement of the abutment with the fixture. The abutment is removably affixed to the fixture by a screw having a threaded end portion and a driven end portion. The threaded end portion is passed through the abutment and threaded in the hollow of the fixture. The driven end portion of the screw is cooperable with a driving tool, such as a screwdriver and engages the abutment, holding the abutment in place against the fixture.

In a presently preferred embodiment, the abutment comprises a divergent segment and a head segment, the segments both having a frusto-conical shape. The smaller end of the divergent segment engages distal end portion of the fixture, while the larger end of the divergent segment is attached to the smaller end of the head segment. The smaller end of the head segment being smaller than the larger end of the divergent segment creates a shoulder at their juncture. The axis of the divergent and head segments are in alignment with the axis of the fixture.

The system additionally comprises a tooth analogue releasibly engagable with the abutment. In a presently preferred embodiment the analogue comprises a crown having a hollow interior adapted to fit on the head section of the abutment. The crown additionally has an opening extending laterally through the sidewall thereof. The opening is alignable with the threaded hollow in the side of the abutment. A holding screw secures the crown to the abutment. The screw has a threaded end portion and a driven end portion. The threaded end portion is passed through the opening in the side of the crown and is threaded in the opening in the side of the abutment. The driven end portion cooperable with a driving tool and is engagable within a recess in the sidewall of the crown. With the exception of the crown, all elements of the invention are made of titanium or other rigid substance, compatible with implantation within the body.

The present invention also comprises an improved healing cap and an improved abutment for use in conjunction with the improved healing cap. Instead of being made of one piece construction, the improved healing cap is made of two piece construction. A first part includes a divergent or frusto-conical segment having the desired shape for the gingiva to heal around so that the gingival tissue heals in a contour reverse to the contour of the divergent segment. The second part includes a cylindrical portion having a threaded stem which permits removable engagement with the first part through a threaded hollow in the adjoining end of the divergent segment, and a driven part or screwhead in the second part joined to the cylindrical segment. During the healing, the second part is removed from the first part which remains in the patient so that the healing of the gingiva is not disturbed. The improved abutment comprises a frusto-conical shaped head segment with a threaded stem extending from the large end of the head segment and engagable with the threaded hollow in the frusto-conical segment of the sealing cap which remains in the patient. The tooth analogue is releasibly engagable with the abutment.

The foregoing and other advantageous and distinguishing features of the invention are described in detail below and are recited in the appended claims.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENT

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are demmed to be within the spirit, scope and contemplation of the invention as further defined in the appended claims.

Figure 1:
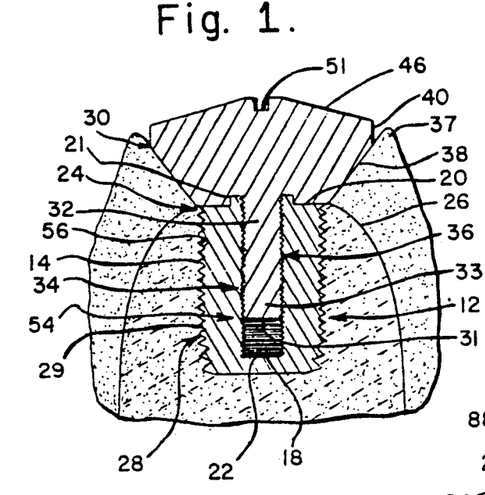
FIG. 1 is a sectional view of a healing cap and fixture of a presently preferred embodiment of the invention showing a portion of the jawbone and gingiva in a broken away configuration.
Figure 2:
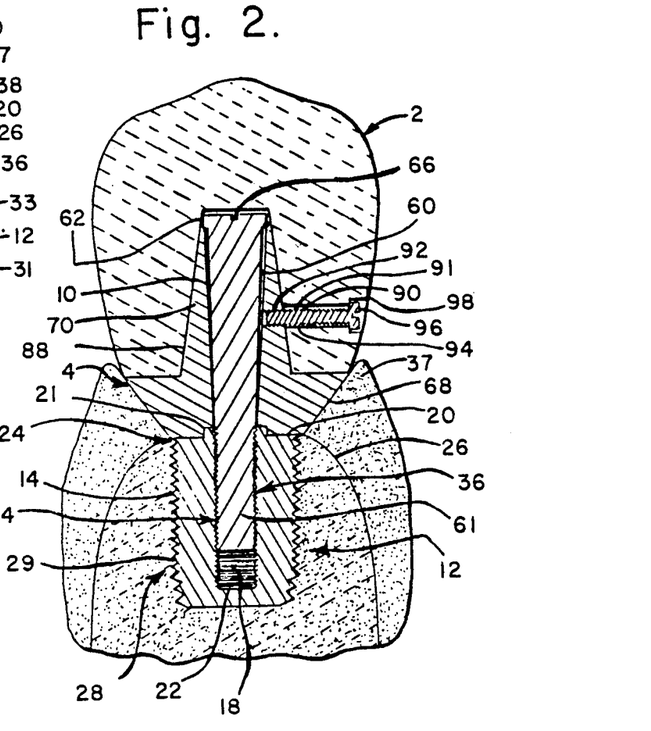
FIG. 2 is a sectional view of a crown, abutment, fixture and holding screws of the presently preferred embodiment of the invention showing a portion of the jawbone and gingiva in a broken away configuration.

Referring now to FIGS. 1 & 2, the present invention is a method and a system of providing a tooth analogue for one or more missing teeth. The tooth analogue may comprise a removable full denture. In a presently preferred embodiment of the invention the analogue comprises a crown 2 removably affixed to an abutment 4. According to the preferred method of installing the analogue in the mouth of a patient, a socket is prepared in the alveolus of the jawbone where a tooth has been extracted or otherwise lost. A conventional fixture 12 is implanted in this area. An exemplary fixture is roughly cylindrical in shape and possesses a threaded surface 14. The fixture 12 includes a hollow portion 18 which extends from the upper surface 20 of the fixture toward the lower surface 22 thereof. The fixture is implanted such that the distal end portion 24 of the fixture extends to the outer surface of the jaw bone 26. The proximal end portion 28 of the fixture extends into the jaw bone 26 as far as is necessary for a satisfactory implantation. In one embodiment, the jawbone is drilled and threaded in preparation for receiving the fixture. During implantation, the threaded surface 14 of the fixture 12 threadingly engages the threaded surface 29 of the jaw bone 26.

After implantation of the fixture 12, a cover screw is threaded into the fixture (not shown) to seal it during the period in which bone is growing about the proximal portion 28 of the fixture. The gingival tissue 37 above the fixture is closed according to procedures well known in the art. Upon completion of osseointergration of the fixture 12, the gingival tissue 37 above the fixtures is reopened and the cover screw is removed. The healing cap 30 is then threaded into the fixture and held in place by a stem 31. The stem has a distal end portion 32, and a proximal end portion which together have a threaded surface 34. The threaded surface 34 is engaged with a threaded surface 36 within the hollow portion 18 of the fixture to hold the healing cap 30 in place. The fixture 12 has a raised lip 21 around the opening of the hollow 18 in the distal end portion 24 of the fixture. The lip 21 may be circular or hexagonal in shape. The lip fits within an appropriately configured socket 39 of the healing cap 30. The engagement of the lip within the socket provides additional support to the engagement of the healing cap 30 to the fixture 12.

The healing cap 30 is additionally configured to allow the gingival tissues 37, surgically displaced during removal of the cover screw to heal around the cap in a shape which is dimensionally similar to the tooth previously removed or lost. The proper contouring of the gingival tissues 37 during their healing is necessary to assure a tight fit between the abutment and the gingiva. This tight fit provides improved esthetics for the completed restoration.

Referring additionally now to FIGS. 3-6, preferred healing caps 30 may be configured in differing diameters, heights and emergence profiles to permit the gingival tissues 37 to be guided in healing to a proper form, commensurate with that desired at the completion of the restoration.

Figure 3:
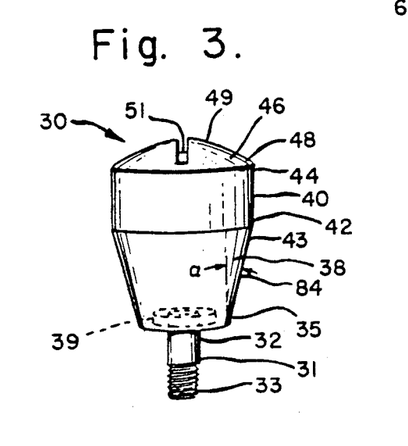
FIG. 3-6 are side elevation views of preferred healing caps of the present invention.
Figure 4:
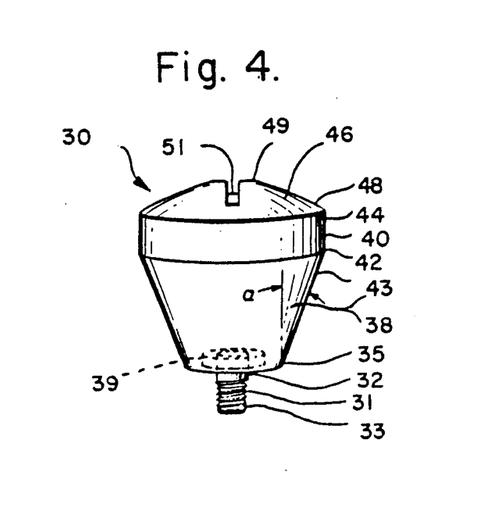

Details of three section healing caps 30 are shown in FIGS. 3 & 4. The caps have a frusto-conical section 38, the smaller end 35 of which is attached to the distal end 32 of the stem 31. A cylindrical section 40 extends away from the frusto-concical section 38, having a proximal end 42 attached to the larger end 43 of the frusto-conical section. A screw head segment 46 terminates the healing cap 30, having a proximal end 48 which is attached to the distal end 44 of the cylindrical section 40. The screw head segment 46 also has a driven end 49 cooperable with a driving tool. The driven end is preferably a slot 51 transverse to the long axis of the healing cap 30, which may be driven by a blade screwdriver.

Figure 5:
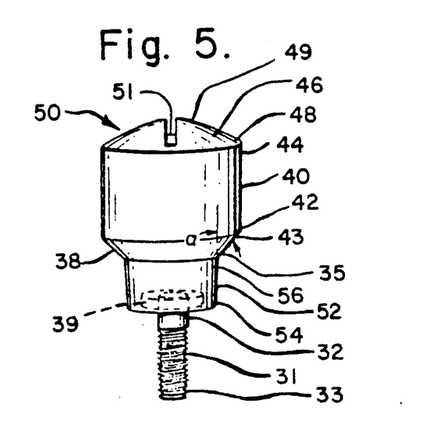
Figure 6:
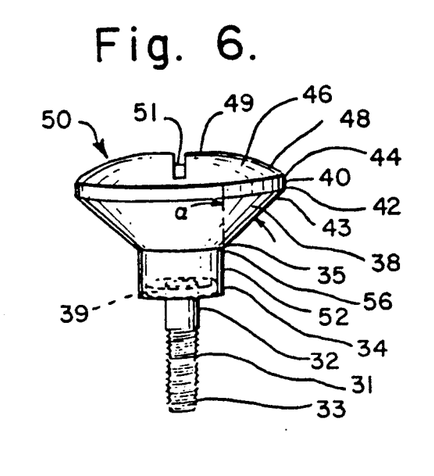

Four section healing caps 50 are shown in FIGS. 5 & 6. These caps have the same elements as the three section caps 30 with the addition of a cylindrical shaped base 52. The base 52 is used to fill the space between the surface of the jaw bone and the distal portion 24 of the fixture 12 when the surface of the jaw bone, after healing about the fixture, extends above the distal portion of the fixture. The base 52 has a proximal end portion 54 and a distal end portion 55. The proximal end portion 54 is attached to the distal end portion 32 of the stem 31, and the distal end portion 55 is attached to the smaller end 35 of the frusto-conical section.

The long axes of the segments 38, 40, 46, 52 and the stem 31 of the healing caps 30, 50 are preferably aligned.

At the juncture of the segments 52, 38, 40 & 46, the circumference of each segment is preferably the same as that of each adjoining segment.

The healing caps 30 & 50 are preferably made of a one piece construction.

After placement of the fixture 12 in the jaw bone 26 and a healing cap 30 or 50 through the gingival tissue 37, the gingiva is sutured about the cap. The fixture and cap are premitted to remain in place until a tooth analogue has been made and is ready for insertion into the fixture. This requires a period of eight weeks or longer. When the tooth analogue is ready for insertion the cap is removed from the fixture 12 and replaced with a tooth analogue including an abutment 4, 6, or 8.

Referring now to FIGS. 2 & 7-9 abutments 4, 6 & 8 are provided having different emergence profiles, in harmony with those of the healing caps 30, 50.

Figure 7:
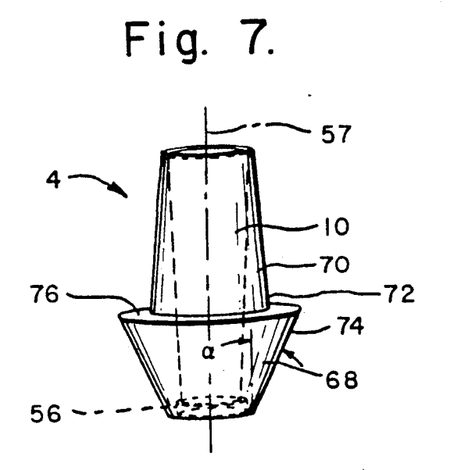
FIG. 7-9 are side elevation views of preferred abutments of the present invention.
Figure 8:
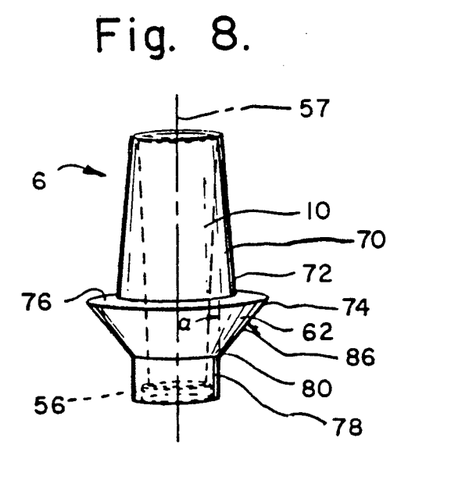
Figure 9:
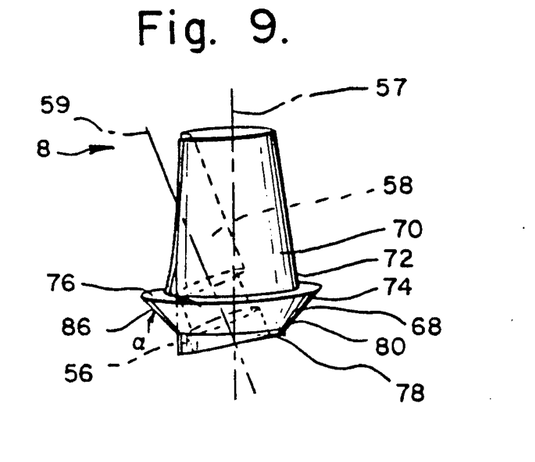

The abutment 4, 6, 8 has a socket 56 adapted to fit the lip 21 on the distal end portion 24 of the fixture 12. The engagement of the lip 21 and the socket 56 provides resistance to shear forces resulting from mastication. Referring to FIGS. 7 & 8, the abutments 4 & 6 have a hollow 10, extending from the socket 56, through the interior of the fixture, centered about the long axis 57 of the abutments 4 & 6. As shown in FIG. 9, a hollow 58 of the abutment 8 is symmetrical about an axis 59 offset from the long axis 57 of the abutment. The offset of the hollow 58 is selected to accommodate a malaligned implanted fixture, or to aid in paralleling abutments for fixed partial dentures. The hollow 58 may emerge partially or fully from the sidewall of the abutment.

Referring again to FIG. 2, the abutment 4 is secured to the fixture 12 by a screw 60 having a threaded end portion 61 and a driven end portion 62. The screw is passed through the abutment hollow 10 and engaged with the threaded surface 36 within the fixture 12. The driven end portion 62 of the screw 60 is preferably a slot 66, transverse to the long axis of the screw, which is cooperable with a blade screwdriver.

Referring now to FIGS. 7-9, the abutments 4, 6, & 8 are comprised of a divergent segment 68, and a head segment 70, both segments having a frusto-conical shape. The larger end 72 of the head segment 70 is affixed to and extends outward from the larger end 74 of the divergent segment 68. The larger end 74 of the divergent segment 68 is larger than the larger end 72 of the head segment 70 thereby creating a shoulder 76 at their juncture. This shoulder provides a surface through which chewing forces from the crown 2, or other tooth analogue, are transferred to the abutment 4, 6, 8.

The abutments 6 & 8 additionally comprise a cylindrically shaped base 78, as shown in FIGS. 8 & 9. The base is joined to and extends from the smaller end 80 of the divergent segment 68. The end 82 of the base 78 is normal to the axis of the hollow 10, 58.

The long axes 57 of the abutments in FIGS. 7, 8 & 9 are preferably in alignment, and the base 78 and the divergent segment 68 are preferably of the same circumference at their juncture. The abutments 4, 6, 8 are preferably made of a one piece construction. To provide the best fitting of the gingival tissues 37 with the abutment 4, 6, 8, the sidewall 84 of the frusto-conical segment of the healing cap 30, 50 and the sidewall 86 of the divergent segment 68 of the abutment, preferably extend outward from the smaller end of the segments at an angle, angle "a" as shown in FIGS. 3, 7 & 8, of between 45 degrees and 65 degrees to the long axis of the segment.

A feature of the use of a screw 60 to secure the abutment 4, 6, 8 to the fixture 12 is that the divergent segment 68 can be prepared in the same manner as a natural tooth, with reduction of the occlusal, and proximal surfaces of the abutment as necessitated by the situation. Additionally, axial reduction of the abutment may be performed to facilitate fabricating anatomically correct restorations. Axial reduction also permits separation from adjacent teeth or implants, and varying cervical contours as required for tissue health and aesthetic appearance. Referring again to FIG. 2, the crown 2 is comprised of elements well known in the dental arts. The crown 2 has a hollow interior 88 adapted to fit on the head 70 of the abutment 4. The crown 2 may be releasably attached to the abutment by a dental crown adhesive or by a screw. When the screw attachment method is used, a screw 90 is passed through an aperture 91 in the side of the crown. The abutment 4 has a threaded hollow 92 in its sidewall extending into the hollow 10 of the abutment. The screw 90 comprises a threaded end portion 94 and a driven end portion 96. The screw is passed through the aperture 91 and the threaded end protion 94 is engaged in the threaded hollow 92. The side of the crown additionally has a recess 98 which receives the driven end portion 96.

With the exception of the crown 2, all elements of the invention are preferably fabricated of pure titanium, but may be made of other biocompatible materials.

The dental implant system of the present invention provides for development of proper gingival tissue form resulting in more aesthetically and functionally desirable tissue contours at the time of and following thooth analogue connection. The system also allows modification and adaptation of the abutment 4, 6, 8 to meet intraoral demands in a manner similar to that used in the preparation and restoration of natural teeth. In view of the foregoing description of the invention in accordance with the requirements of the patent statutes, those skilled in the relevant arts will have no difficulties making changes and modifications in the different described elements of the invention in order to meet their specific requirements or conditions. For example, those elements having a driven end may comprise a socket cooperable with an allen wrench. Multiple as well as single restorations may be accomplished. Fixed full or partial dentures or removable prostheses may constitute the tooth analogues. Such changes and modifications may be made with out departing from the scope and spirit of the present invention.

In operation, the fixture 12 remains in the jawbone 26 and the healing cap 30 or 50 is threaded into the fixture and held in place by stem 31. As previously described, the threaded surface 34 of stem 31 is engaged with the threaded surface 36 within the hollow portion 18 of fixture 12 to hold the healing cap 30 or 50 in place. The gingival tissues 37 are then given time (usually at least eight weeks) to heal around the healing cap 30 or 50. The proper contouring of the gingival tissues 37 during their healing is necessary to assure a tight fit between the abutment and the gingiva. During this time, osseointergration of the fixture 12 to the jawbone 26 also takes place. When the time is ready to test fit a crown 2, which initially is a temporary crown and subsequently a permanent crown, it is necessary to entirely remove the healing cap 30 or 50 and replace it with the abutment 4, 6 or 8 in the manner previously described. By this time, the regrown gingival tissues 37 have conformed to the shape of the frusto-conical section 38 of healing cap 30 or 50. Therefore, when the healing cap 30 or 50 is removed, at least some damage such as bruising and possibly some tissue removal is imparted to the regrown portion of gingival tissues 37 adjacent the frusto-conical section 38. Therefore, after the temporary crown is fitted, it is necessary to once again reinsert the healing cap 30 or 50 and the gingival tissues 37 must again be given time to regrow. Due to the bruising or tissue removal, the gingival tissues 37 may not properly regrow in the manner originally formed against the frusto-conical section 38. This results in a delay of several additional weeks. In addition, this procedure must be repeated if it is necessary to refit the temporary crown and further must be repeated when it is time to fit the permanent crown.

Therefore, an improvement is required wherein at least the frusto-conical portion 38 of healing cap 30 or 50 remains threaded into the jaw 26 and the frusto-conical portion 38 remains in its position within the regrown gingival tissues 37, thereby substantially reducing the trauma caused to the gingival tissues 37 when the temporary crown and later the permanent crown is fitted. An improved healing cap 130 and mating abutment member is illustrated in FIGS. 10 through 13. As with the healing caps illustrated in FIGS. 3 through 6, the improved healing cap 130 may be configured in differing diameters, heights and emergence profiles to permit the gingival tissues 37 to be guided in healing to a proper form, commensurate with that desired at the completion of the restoration. In addition, although the improved healing cap 130 is illustrated as a three section cap comparable to the healing caps illustrated in FIGS. 3 and 4, it can also be composed in the form of the four section healing caps illustrated in FIGS. 5 and 6 with the addition of a cylindrical shaped base beneath the frusto-conical section.

Figures 10, 11, 12, 13:
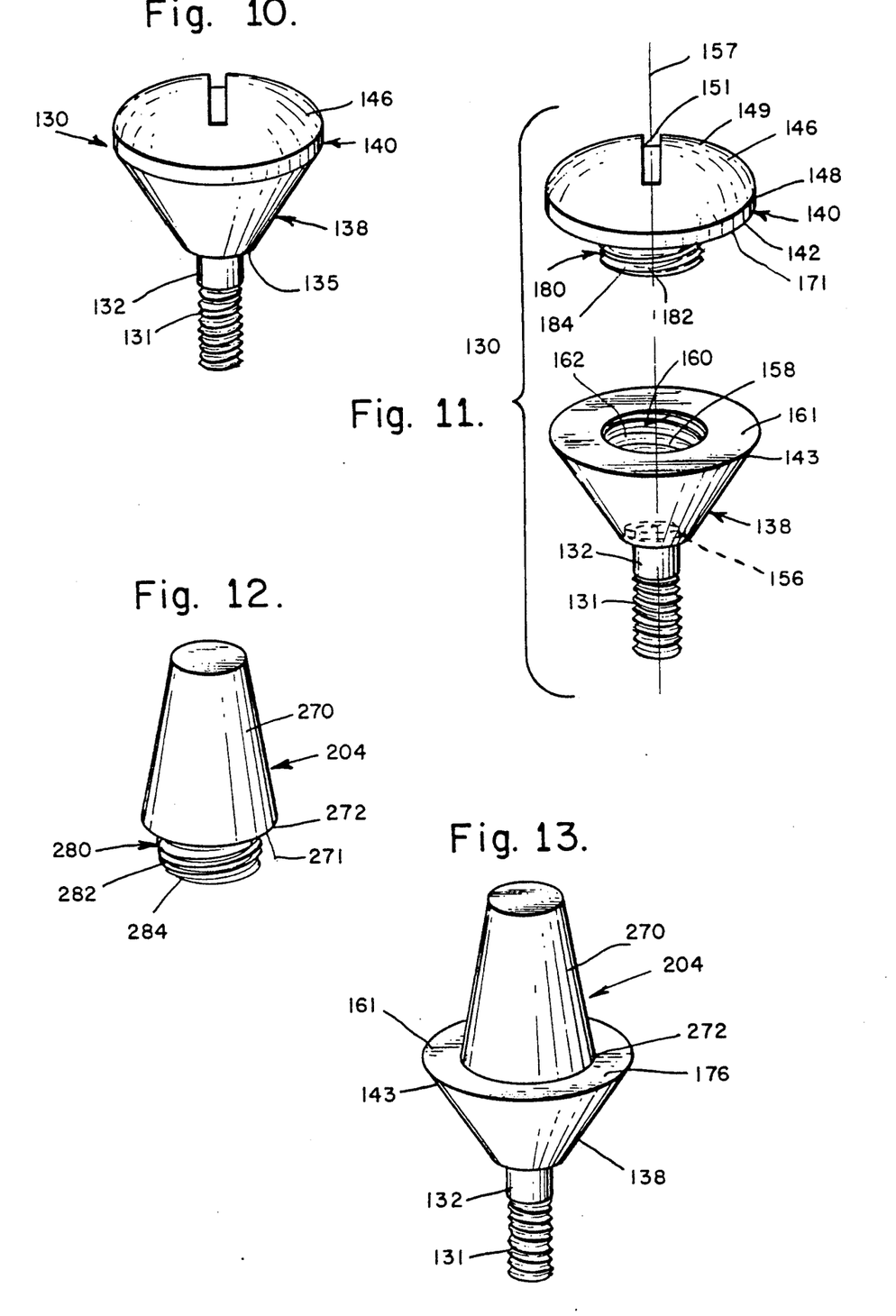
FIG. 10 is a perspective view of an improved healing cap of the present invention.
FIG. 11 is a perspective view of the improved healing cap of the present invention with the top of the healing cap unscrewed from the base of the healing cap.
FIG. 12 is a perspective view of an improved abutment of the present invention.
FIG. 13 is a perspective view the improved abutment illustrated in FIG. 12 screwed into the base of the improved healing cap illustrated in FIG. 13.

The critical feature of novelty in the improved healing cap 130, regardless of whether it is a three section healing cap comparable to those illustrated in FIGS. 3 and 4 or a four section healing cap comparable those illustrated in FIGS. 5 and 6, is that instead of being of one piece construction which is the design of all four healing caps in FIGS. 3 through 6, the improved healing cap is made of two piece construction. Referring to FIGS. 10 and 11, the improved healing cap 130 has a frusto-conical section 138, the smaller end 135 of which is attached to the distal end 132 of stem 131. Frusto-conical section 138 has a flat upper surface 161 which is transverse to the larger end 143 of the frusto-conical section 138. Frusto-conical section 138 further comprises a hollow 158 having an interior wall 160 which has threads 162 in wall 160. Hollow 158 extends transversely to flat supper surface 161 and is axially aligned with frusto-conical section 138.

The improved healing cap 130 also has a separate cylindrical section 140 integral with the screw head segment 146. The cylindrical section 140 has a lower surface 171 which is generally flat and perpendicular to the proximal end 142 of cylindrical section 140. A stem 180 is integral with and aligned transversely to lower surface 171 and is aligned axially with cylindrical section 140. Stem 180 has threads 182 on its outer surface 184. The stem 180 is aligned with hollow 158 and the threads 182 of stem 180 are mating threads With the threads 162 of hollow 158. Therefore, when threaded together, flat upper surface 161 of frusto-conical sectional 138 lies against lower flat surface 171 of cylindrical section 140 and the proximal end 142 of cylindrical section 140 lies adjacent the large end 143 of frusto-conical section 138. The frusto-conical section 138 has a socket 156 which is configured to permit raised lip 21 of fixture 12 to fit within the socket 156, in the manner previously described. The lip 21 is circular in shape and the socket 156 is appropriately configured to the shape of the lip 21. The engagement of the lip within the socket provides additional support to the engagement of the healing cap 130 to the fixture 12.

The screw head segment 146 terminates the healing cap 130, having a proximal end 148 which is attached to the distal end 144 of the cylindrical section 140. The screw head segment 146 also has a driven end 149 cooperable with a driving tool. The driven end is preferably a slot 151 transverse to the long axis of the healing cap 130, which may be driven by a blade screwdriver.

Therefore, the improved healing cap 130 is of two piece construction, with the cylindrical section 140 and screw head segment 146 forming one section and the frusto-conical section 138 forming the second section, with the two sections removably screwed together in the manner previously described.

The improved abutment 204 is illustrated in FIG. 12. The improved abutment 204 has a head segment 270 which is frusto-conical in shape. The larger or proximal end 272 of head segment 270 has a generally flat lower surface 271, which is generally perpendicular to the proximal end 272 of head segment 270. A stem 280 is integral with and aligned transversely to lower surface 271 and is aligned axially with head segment 270. Stem 280 has threads 282 on its outer surface 284. The stem 280 is preferably identical to stem 180 of cylindrical section 140 and the threads 282 are preferably identical to threads 182. Therefore, when stem 282 is aligned with hollow 158 the threads 282 of stem 280 are mating threads with the threads 162 of hollow 158. As illustrated in FIG. 13, when threaded together, flat upper surface 161 of frusto-conical sectional 160 lies against lower flat surface 271 of head segment 270. In the preferred embodiment, the diameter of proximal end 142 of cylindrical section 140 was approximately equal to the diameter of the distal or large end 143 of frusto-conical section 138 and the diameter of proximal end 272 of head segment 270 is smaller than the diameter of the large end 143 of frusto-conical section 138. Therefore, when head segment 270 is screwed into frusto-conical section 138, a shoulder 176 is created at their juncture and on the portion of flat surface 161 which remains exposed after head segment 270 is screwed in place.

Therefore, the improvement in this design over the one piece healing cap 30 or 50 and one piece abutment 4, 6, 8, is apparent. The improved healing cap 130 is inserted into the fixture 12 with stem 131 threaded into fixture 12. As with the previous embodiment, the lip 21 of fixture 12 is accommodated into socket 156. The gingival tissues 37 regrow as before and conform to the shape of the frusto-conical section 138. At this time, after the gingival tissues 37 have regrown and it is necessary to replace the healing cap with an abutment, instead of having to remove the entire healing cap with the attendant potential for damage to regrown gingival tissue 37, the separate cylindrical section 140 and screw head segment 146 is unscrewed from the frusto-conical section 138. The screw head segment 146 and cylindrical section 140 rests at the distal end of the gingival tissues 37 and therefore very little if any of the regrown gingival tissues 37 are disturbed. After the cylindrical section 140 and head section 146 are unscrewed, the improved abutment 270 is screwed into the frusto-conical section 138. As a result, the shape of the improved abutment 130 screwed into the frusto-conical section 138 is identical to the shape of the prior abutments 4, 6 or 8 but without the necessity of having to remove the frusto-conical section 138 and disturb the surrounding gingival tissues 37.

The hollow 158 of frusto-conical section 138 is centered about long axis 157 of frusto-conical section 138. The threaded stem 280 being threaded into threaded hollow 158 eliminates the need for the long screw 60 of the previous embodiment. In addition, through this improved embodiment, it is not necessary to unscrew stem 131 from the fixture 12 and therefore this bond also does not have to be broken.

After the temporary crown has been fitted, it can be left in place on the head section 270 of abutment 204 and it is not necessary to replace the cylindrical section 140 and screw head segment 146 since no gingival tissues 37 have been disturbed and no regrowth time is required.

As with the embodiments of the abutments illustrated in FIGS. 7 through 9, the angle "a" of the frusto-conical section 138 can vary between 45 degrees and 65 degrees, depending on the specific configuration of the jaw and tissues of the individual patient. The abutment 130 can also undergo axial reduction as with the prior abutment embodiments to facilitate fabricating anatomically correct restorations. As with prior abutment embodiments, axial reduction also permits separation from adjacent teeth or implants, and varying cervical contours as required for tissue health and aesthetic appearance.

The crown is fitted over abutment 204 and over head 270 in the same manner as it was fitted over head 70 of prior abutment embodiments, in the manner illustrated in FIG. 2. The crown 2 has a hollow interior 88 adapted to fit on the head 270 of the abutment 204. As with the previous embodiment, the crown 2 may be releasably attached to the abutment by a dental crown adhesive or by a screw. As with the embodiment illustrated in FIG. 2., when the screw attachment method is used, a screw 90 is passed through an aperture in the side of the crown. The head 270 has a threaded hollow comparable to 92 in its sidewall extending into the head 270. The screw 90 comprises a threaded end portion 94 and a driven end portion 96. The screw is passed through the aperture 91 and the threaded end portion 94 is engaged in the threaded hollow 92. The side of the crown additionally has a recess 98 which receives the driven end portion 96.

All elements of the improved healing cap 130 and the improved abutment 204 are preferably made of titanium, but may also be made of other biocompatable materials.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus is intended only for illustration and or disclosure of an operative embodiment and not to show all of the various forms of modification in which the invention might be embodied or operated.

The invention has been described in considerable detail in order to comply with the patent laws by providing full public disclosure of at least one of its forms. However, such detailed description is not intended in any way to limit the broad features or principles of the invention or the scope of patent monopoly to be granted.

What is claimed is:

1. A dental implant system implantable in the gingival tissue and the alveolus of the jaw bone comprising:
  a. an implantable fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from an opening in the distal end portion towards the proximal end portion, the hollow having threads along at least a portion of its length;
  b. means for sealing the hollow portion of the fixture during a period after implantation in which the jaw bone is growing about the proximal portion of the fixture;
  c. means for providing a predetermined contour to the gingival tissue adjacent the distal end of the fixture, such that the gingival tissue re-heals in a contour reverse to that of the contour of said means;
  d. a tooth analogue;
  e. abutment means for supporting the tooth analogue;
  f. means for releasibly attaching the tooth analogue to the abutment means;
  g. said contour means being a two part healing cap further comprising,
    (i) a first part including a stem having proximal and distal end portions, the proximal portion of the stem having threads which are threadable within the hollow of the implantable fixture, and a frusto-conical segment, the smaller end of the segment being attached to the distal end of the stem, with the axis of the segment being in alignment with the axis of the stem, the frusto-conical segment further including a hollow extending from an opening in the larger end of the segment toward the smaller end of the segment, the hollow having threads along at least a portion of its length,
    (ii) a second part including a cylindrical segment having proximal and distal ends, the proximal end having a stem extending transversely to the proximal end, the axis of the stem aligned with the axis of the cylindrical segment, the stem having a threaded surface which is threadable within the hollow of the frusto-conical segment, and a screw head segment having a proximal end and a driven end, the driven end cooperable with a driving tool, the proximal end being attached to the distal end of the cylindrical segment, with the axis of the screw head segment being in alignment with the axis of the cylindrical segment; and h. said abutment means further comprising a head segment having a frusto-conical shape, the larger end of the head segment attached to a stem extending transversely to the larger end, the axis of the stem aligned with the axis of the head segment, the stem having a threaded surface which is threadable within the hollow of the frusto-conical segment of said healing cap;

i. whereby the stem of said healing cap is threaded into the hollow of said fixture and the gingival tissue re-heals in a contour reverse to that of the contour of the frusto-conical portion of the healing cap, and thereafter the second part of the healing cap is unscrewed from the first part of the healing cap and the stem of said abutment means is screwed into the frusto-conical portion of the healing cap and the tooth analogue is attached to the abutment means.

2. The dental implant system of claim 1 wherein the tooth analogue comprises a crown having a hollow interior adapted to fit on a portion of the abutment.

3. The dental implant system of claim 2 wherein the means for releasibly attaching the crown to the abutment comprises:
a. a threaded hollow in the side of the abutment means;
b. an opening extending laterally through the side of the crown, the crown opening alignable with the threaded hollow in the side of the abutment means; and
c. a holding screw having a threaded end portion and a driven end portion, the threaded end portion passing through the opening in the side of the crown and threaded in the opening in the side of the abutment, the driven end portion cooperable with a driving tool and engagable with the crown.

4. The dental implant system of claim 1 wherein the means for releasibly attaching the tooth analogue to the abutment includes an adhesive.

5. The dental implant system of claim 1 wherein said healing cap additionally comprises a base, the base having a cylindrical shape with proximal and distal ends, the proximal end of the base being attached to the distal end portion of said stem, and the distal end of the base being attached to the smaller end of said frusto-conical segment, with the axis of the base being in alignment with the axis of said stem and said frusto-conical segment.

6. The dental implant system of claims 1 or 5 wherein regarding said healing cap, the exterior of the sidewall of said frusto-conical segment extends outward from the smaller end of said segment at an angle of between 45 degrees and 65 degrees to the axis of said segment.

7. The dental implant system of claims 1 or 5 wherein regarding said healing cap, at the juncture between said screwhead segment and said cylindrical segment, the circumference of said screwhead segment is the same as the circumference of said cylindrical segment.

8. The dental implant system of claims 1 or 5 wherein regarding said healing cap, when the first part is screwed into the second part, at the juncture between said cylindrical segment and said frusto-conical segment, the circumference of said cylindrical segment is the same as the circumference of said frusto-conical segment.

9. The dental implant system of claim 1 wherein the larger end of the frusto-conical segment of said healing cap is larger than the larger end of the head segment of said abutment means thereby creating a shoulder at their juncture.

10. A two part healing cap for use with an implantable fixture having an open end and a threaded hollow, the healing cap comprising:
a. a first part further comprising,
 (i) a stem having proximal and distal end portions, the proximal end portion being threadable within the hollow of the implantable fixture thereby sealing the fixture;
 (ii) a divergent segment having frusto-conical shape, the smaller end of the segment being attached to distal end of the stem, with the axis of the segment being in alignment with the axis of the stem;
 (iii) the divergent segment further including a hollow extending from an opening in the larger end of the segment toward the smaller end of the segment, the hollow having threads along at least a portion of its length,
b. a second part further comprising,
 (i) a cylindrical segment having proximal and distal ends, the proximal end having a stem extending transversely to the proximal end, the axis of the stem aligned with the axis of the cylindrical segment, the stem having a threaded surface which is threadable within the hollow of the divergent segment, with the axis of the cylindrical segment being in alignment with the axis of the divergent segment, and
 (ii) a screw head segment having a proximal end and a driven end, the driven end cooperable with a driving tool, the proximal end being attached to the distal end of the cylindrical segment, with the axis of the screw head segment being in alignment with the axis of the cylindrical segment.

11. The healing cap of claim 10 additionally comprising a base, the base having a cylindrical shape with proximal and distal ends, the proximal end of the base being attached to the distal end portion of the stem, and the distal end of the base being attached to the proximal end of the divergent segment, with the axis of the base being in alignment with the axis of the stem and the divergent segment.

12. The healing cap of claims 10 or 11 wherein the exterior of the sidewall of the divergent segment extends outward from the smaller end of the segment at an angle of between 45 degrees and 65 degrees to the axis of the segment.

13. The healing cap of claims 10 or 11 wherein, at the juncture of between said screwhead segment and said cylindrical segment, the circumference of said screwhead segment is the same as the circumference of said cylindrical segment.

14. The healing cap of claims 10 or 11 wherein, when the first part of the healing cap is screwed into the second part of the healing cap, at the juncture between said cylindrical segment and said frusto-conical segment, the circumference of said cylindrical segment is the same as the circumference of said frusto-conical segment.

15. A method for implanting a tooth in the gingival tissue and the alveolus of the jawbone comprising:
a. implanting a fixture having proximal and distal end the proximal end portion having means for being embedd in opened gingival tissue and the alveolus of the jaw bone, the distal end portion being accessible from the outer surface of the jaw bone, the fixture being made of a substance perm . healing of the opened gingival tissue and growth of bone about the fixture, the fixture further including hollow extending from the distal end portion toward the proximal end portion, the hollow being threaded along a portion of its length;

b. sealing the hollow portion of the fixture with a cover screw a period after implantation in which the jaw bone is about the proximal portion of the fixture and the opened gingival tissue is healing, thereby preventing the jaw bone entering the fixture;

c. reopening the gingival tissue and removing the cover screw, replacing the screw with a two part healing cap which includes a driven part and a frusto-conical part which provides a predetermined contour to the gingival tissue adjacent distal end of the fixture after the jaw bone has grown about the proximal portion of the fixture, thereby causing gingival tissue to re-heal in a contour reverse to that the frusto-conical portion of the healing cap provided;

d. removing the driven part of the healing cap and replacing it with abutment means engagable with the frusto-conical portion of the healing cap, the abutment means used for supporting a tooth analogue with the implanted fixture; and e. releasibly attaching a tooth analogue to the abutment means.

16. A two part abutment device for use with an implantable fixture having an open end and a threaded hollow, the abutment device comprising:

a. a first part further comprising,
  (i) a stem having proximal and distal end portions, the proximal end portion being threadable within the hollow of the implantable fixture thereby sealing the fixture;
  (ii) a divergent segment having frusto-conical shape, the smaller end of the segment being attached to the distal end of the stem, with the axis of the segment being in alignment with the axis of the stem;
  (iii) the divergent segment further including a hollow extending from an opening in the larger end of the segment toward the smaller end of the segment, the hollow having threads along at least a portion of its length; and b. a second part being a head segment having a frusto-conical shape, the larger end of the head segment attached to a stem extending transversely to the larger end, the axis of the stem aligned with the axis of the head segment, the stem having a threaded surface which is threadable within the hollow of the divergent segment, with the axis of the head segment being aligned with the axis of the divergent segment.

17. The abutment device of claim 16 wherein when the first part is screwed into the second part, the larger end of the divergent segment is larger than the larger end of the head segment thereby creating a shoulder at their juncture.

* * * * *